(12) United States Patent
Schilling

(10) Patent No.: US 8,894,968 B2
(45) Date of Patent: Nov. 25, 2014

(54) COMPOSITIONS EMITTING POSITRONS AND CONTAINING INORGANIC PARTICLES, AND USE THEREOF IN MEDICINE, ESPECIALLY FOR DIAGNOSTIC PROCESSES

(75) Inventor: Kristian Schilling, Berlin (DE)

(73) Assignee: nanoPET Pharma GmbH, Berlin (DE)

( * ) Notice: Subject to any disclaimer, the term of this patent is extended or adjusted under 35 U.S.C. 154(b) by 877 days.

(21) Appl. No.: 12/665,624

(22) PCT Filed: Jun. 20, 2008

(86) PCT No.: PCT/EP2008/057917
§ 371 (c)(1), (2), (4) Date: Jul. 6, 2010

(87) PCT Pub. No.: WO2009/000785
PCT Pub. Date: Dec. 31, 2008

(65) Prior Publication Data
US 2010/0272637 A1    Oct. 28, 2010

(30) Foreign Application Priority Data

Jun. 22, 2007  (EP) ..................... 07110908

(51) Int. Cl.
*A61K 9/10* (2006.01)
*A61K 51/00* (2006.01)
*A61K 51/12* (2006.01)

(52) U.S. Cl.
CPC .................................. *A61K 51/1255* (2013.01)
USPC ......... 424/1.25; 424/1.11; 424/9.32; 424/9.4; 424/489

(58) Field of Classification Search
USPC ......... 424/1.1, 1.11, 1.29, 1.33, 1.37, 4, 9.32, 424/9.4, 489, 684, 1.25; 600/1; 606/27
See application file for complete search history.

(56) References Cited

U.S. PATENT DOCUMENTS

| | | | | |
|---|---|---|---|---|
| 5,122,363 | A * | 6/1992 | Balkus et al. ................ | 424/9.31 |
| 5,948,384 | A * | 9/1999 | Filler .......................... | 424/1.29 |
| 2003/0228260 | A1 | 12/2003 | Filler | |
| 2007/0112339 | A9 * | 5/2007 | Ivkov .............................. | 606/27 |
| 2007/0264199 | A1 * | 11/2007 | Labhasetwar et al. ....... | 424/9.32 |

FOREIGN PATENT DOCUMENTS

| | | |
|---|---|---|
| WO | 2006064451 A2 | 6/2006 |
| WO | 2006064453 A2 | 6/2006 |
| WO | PCT2008057917 R | 6/2008 |

OTHER PUBLICATIONS

Marco Pagani et al., Alternative Positron emission tomography with non-conventional positron emitters: effects of their physical porperties on image quality and potential clinical applicaitons. European Journal of Nuclear Medicine, vol. 24 (10), 1301-1327, 1997.*
Libor Machala et. al. Amorphous Iron (III) Oxide-Review, J. Phys. Chem. B 2007, 111, 4003-4018.*
Pedro Tartaj et. al. The Preparation of magnetic nanoparticles for application in biomedicine, J. Phys. D: Appl. Phys. 36. (2003), R182-R197.*
D2: Welch M. J and Redvanly C. S.: "Handbook of Radiopharmaceuticals" 2003, John Wiley & Sons, Great Britain, XP002521046.
Forrest. S. et al.: 'Flow patterns in granulating systems' Powder Technology, Bd. 130, 2003, Seiten 91-96, XP007903371.
Peackock K. et al.: '99mTc-Stannous Colloid White Cell Scintigraphy in Childhood Inflammatory Bowel Disease'.
Boehmert & Boehmert. "Written Opinion." PCT/EP2008/057917. Examiner: Unknown. Applicant: Nanopet Pharma GmbH. Mailed Jan. 21, 2010.

* cited by examiner

*Primary Examiner* — Nissa Westerberg
*Assistant Examiner* — Jagadishwar Samala
(74) *Attorney, Agent, or Firm* — Millen, White, Zelano & Branigan, P.C.

(57) ABSTRACT

The invention relates to pharmaceutical agents containing a particulate inorganic matrix having a diameter of from 0.1 nm to 100 μm, preferably 1 nm to 10 μm, particularly preferably 1 nm to 1 μm, such as, for example, topaz, $(Al_2F_2)[SiO_4]$, and chiolite, $Na[Al_3F_4]$, preferably wavellite, $Al_3(PO_4)_2(OH,F)_2$, calcium carbonate, $CaCO_3$, maghemite, $\gamma\text{-}Fe_2O_3$, particularly preferably zeolites, gen. formula $M_n[(AlO_2)_x(SiO_2)_y]$ (M=metal, e.g. Na), magnetite, $Fe_3O_4$, and barium sulphate, $BaSO_4$, and very particularly preferably gallium phosphate, $GaPO_4$, apatite or fluorohydroxyapatite, $Ca_5(PO_4)_3(OH,F)=3Ca_3(PO_4)_2{*}Ca(OH,F)_2$, and fluorspar, $CaF_2$, which, in addition to the natural isotope distribution of the structure type-forming elements of the anions and cations, also contain medically usable contents of positron-emitting nuclides, such as, for example, $^{15}$O, [30]P, $^{13}$N, preferably [65]Ga, $^{11}$C, particularly preferably [13]Ba, [26]Al, and very particularly preferably $^{68}$Ga and $^{18}$F, the preparation thereof, and the use of these composition in medicine, particularly preferably in diagnostic imaging, in particular positron emission tomography (PET), on animals and humans, and in vitro diagnostics.

20 Claims, 4 Drawing Sheets

COMPOSITIONS EMITTING POSITRONS AND CONTAINING INORGANIC PARTICLES, AND USE THEREOF IN MEDICINE, ESPECIALLY FOR DIAGNOSTIC PROCESSES

Of the more than 50 known positron emitters, only a few can be employed in medicine. Currently the most important PET nuclides are $^{18}$F, $^{11}$C, $^{13}$N and [15]O. They are distinguished by their extremely short half-life, which ranges from approx. 110 min for $^{18}$F up to about 2 min for [15]O.

These short half-lives indeed make enormous demands on the provision of these substances and measurement evaluation, but nevertheless bring to the patient the advantage of low exposure to radiation because of a very short exposure time.

A further advantage of these PET nuclides is that in principle any organic molecule can be radioactively labelled with them. Every organic molecule has one or more carbon atoms (as a rule: [12]C), one of which can be replaced by an $^{11}$C; many organic molecules moreover carry an oxygen or nitrogen atom.

Although fluorine occurs relatively rarely in natural and synthetic compounds, it can nevertheless be incorporated into organic molecules relatively easily by replacement of hydrogen atoms or hydroxyl groups. Since the comparatively long half-life of $^{18}$F facilitates the preparation and use of $^{18}$F-labelled radiopharmaceuticals, it is the PET nuclide which is employed the most frequently.

Thus above all compounds which are endogenous to the body, such as carbohydrates, amino acids, enzymes, hormones or neurotransmitters, but also other pharmaceuticals can be labelled with positron emitters without the structure thereof and thus the biochemical and pharmacological properties thereof changing substantially. The absolute amounts of the labelled substances administered are so low (in the micromolar range) that the physiological concentrations are not influenced.

Production of Positron Emitters

Since all positron emitters used medically have extremely short half-lives, they cannot be held in stock but must be prepared individually on site. Because a particle accelerator (often a cyclotron) is necessary for this, there are only few PET centres—usually in larger university hospitals.

The so-called target reaction is to be explained using the example of production of $^{18}$F ions. Here, an accelerated proton in the target impinges on an $^{18}$O atom of $^{18}$O-enriched water. A fluorine atom $^{18}$F is formed with emission of a neutron:

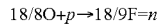

$$18/8O + p \rightarrow 18/9F = n$$

This is negatively charged and leaves the target as aqueous $^{18}$F-fluoride solution.

[18]Fluorine without doubt plays by far the greatest role in the preparation of PET radiopharmaceuticals. [18]F is also the only positron emitter, which, to a certain extent, can be transported from a PET centre with a cyclotron to another nuclear medicine facility.

In this context, the radiopharmaceutical can be delivered as ready for administration, or also as the irradiation product (as a rule [18]-fluoride), so that the actual radiochemical synthesis then takes place on site.

The positron emitters $^{11}$C, $^{13}$N and $^{15}$O can be produced only for immediate use in PET centres because of their short half-life.

Radiochemical Synthesis

In the fewest of cases the radionuclide in the form as it is formed in the target of the cyclotron is already the radioactive medicament. It is therefore then incorporated into an organochemical compound (structure from organic chemistry, as opposed to inorganic chemistry).

While the technetium isotope Tc-99m used in scintigraphy is usually bonded as a complex onto a receptor-specific carrier substance, the PET nuclides are integrated into the radiopharmaceutical by a covalent bond.

A chemical synthesis is needed for this, which does not differ from conventional reactions of preparative chemistry inasmuch as radioactive elements and substances have the same chemical properties as their non-radioactive analogues.

However, since the radiation dose emitted by the starting activities as a rule are far above the admissible limit values, almost all routinely prepared PET radiopharmaceuticals are prepared not manually but by remote control with the aid of automatic synthesis modules or by robots.

The functioning principle of all automatic synthesis modules is actually always the same. The synthesis modules allow liquids to be transported from one vessel into another and allow these to be stirred, heated, cooled, concentrated, extracted, (sterile-) filtered and transferred to containers.

Rinsing and cleaning operations required after the synthesis should likewise proceed automatically where possible and should be quick and easy to carry out, so that a renewed synthesis can proceed in the apparatus within a short space of time.

At the end, purification of the product by—likewise automated—preparative HPLC is often necessary. Finally, the aqueous solution of the radiopharmaceutical is rendered isotonic by addition of an appropriate amount of sodium chloride (solution) and forced into the delivery vessel via a sterile filter.

The most important PET radiopharmaceuticals include:
- $^{11}$C-methionine as an important marker in amino acid metabolism,
- 1-$^{11}$C-acetate for cardiac diagnostics,
- $^{15}$O-labelled water for circulatory disorder diagnostics, and
- $^{18}$F-fluoro-DOPA for early diagnosis of Parkinson's disease and other dopaminergic disorders,
- [18]F-2-fluoro-2-deoxyglucose (FDG) is without doubt the most important PET radiopharmaceutical, which is used above all in oncological diagnostics, but also in other fields (see below).

Moreover, an important feature of all the radiopharmaceuticals, in particular PET radiopharmaceuticals, used in human diagnostics is that all the substances have only a single marking with a diagnostically active nuclide. Each molecule can accordingly emit a maximum of one diagnostically usable signal.

Diagnostics in Nuclear Medicine

The prerequisite of all investigations in nuclear medicine is administration of a radioactive substance, the radiopharmaceutical, into the human body. This is usually administered intravenously and initially distributes itself within the blood more or less homogeneously over the entire body.

Because of the biological function of the radiopharmaceutical or its specific affinity for certain substances and receptors, an inhomogeneous redistribution occurs, which can be measured by external detectors or tomographs on the basis of the radioactive radiation and provides conclusions on the functional state of the organs and body regions investigated.

Tumour Diagnostics with FDG-PET

By far the most frequently used PET radiopharmaceutical is [18]F-2-fluoro-2-deoxyglucose, usually abbreviated as FDG. This is a glucose molecule which carries a radioactive $^{18}$F atom instead of an OH groups on C2. After intravenous administration it accumulates above all in cells with an increased glucose requirement.

The body in fact does not distinguish between "normal" glucose and the $^{18}$F-labelled fluorodeoxyglucose. Since in tumour cells of some types of tumour an increased metabolism prevails, they take up more glucose or FDG than non-degenerated cells, so that FDG-PET can locate tumours.

However, an exceptional concentration of the radioactive glucose does not always have to indicate a cancer event. For example, FDG accumulates highly non-specifically in the brain, which on the one hand makes investigation of neurological problems difficult, and also has the consequence of considerable exposure of the brain tissue to radiation.

FDG-PET-assisted diagnosis is moreover successful only in the case of tumour types with an increased glucose uptake, and therefore rules out location of slow-growing tumours.

Measurement Technology

The range of an emitted positron in tissue is at most only a few millimeters, before it meets with an electron and is converted into two γ-quanta flying in diametrically opposite directions. The entire process from emission of the positron to conversion of the masses into the two γ-quanta takes about $10^{-10}$ seconds (0.1 ns).

A coincidence or pair detector is used to detect the γ-quanta by the PET. If each of two individual detectors positioned at a 180° angle record a γ-quantum of defined energy within a very short interval of time of about 10 ns, it is concluded that a positron decay has taken place somewhere on the connecting zone between the two detectors.

In addition to limitations in the field of detector engineering, the intrinsic resolution limit is determined by the average free path length of the positron in the surrounding medium (tissue, tissue fluid, blood etc.). If the electron density in the surroundings of the positron decay could be increased, the probability of interaction of the positron with an electron increases. The average free path length is therefore shortened and the resolution limit can be improved to lower sizes.

Summarizing, the Prior Art has in Particular the Following Disadvantages and Limitations:

The prior art describes only diagnostic agents from the abundance of substances of organic chemistry. Time-consuming, often multi-stage synthesis and purification steps are required for the preparation of the organic substances, which means that because of the low half-lives of the nuclides, the relative yield of diagnostically active product becomes lower with increasing preparation time. The PET diagnostic agent used most, FDG, moreover accumulates highly non-specifically in the brain, which on the one hand makes investigation of neurological problems difficult, and also has the consequence of considerable exposure of brain tissue to radiation. FDG-PET-assisted diagnosis is moreover successful only in the case of tumour types with an increased glucose uptake, and therefore severely limits location of slow-growing tumours. Since the radiopharmaceuticals used according to the prior art in human diagnostics, in particular PET radiopharmaceuticals, have only a single marking with a diagnostically active nuclide, each molecule accordingly can emit a maximum of one diagnostically usable signal. The organic PET radiopharmaceuticals moreover have a similar electron density to the surrounding tissue. The spatial resolution therefore cannot be improved.

The object on which the present invention is based was therefore to provide novel medically, in particular diagnostically usable agents which avoid the disadvantages of the prior art described above.

The subject matter of the present invention is therefore a pharmaceutical agent comprising a particulate inorganic matrix, which in addition to the natural isotope distribution of the structure type-forming elements of the anions and cations, contains contents of positron-emitting nuclides, wherein the number of positron-emitting nuclides per particulate inorganic matrix is preferably greater than or equal to 1.

The possible structure types of the particulate inorganic matrix can include both crystal structures and amorphous structures or mixtures of the two. The term includes both colloids, sols, suspensions, nanosuspensions and amorphous and crystalline particles.

Preferably, the number of medically, in particular diagnostically usable, positron-emitting nuclides per particulate inorganic matrix is 1 to 10,000,000 and particularly preferably 5 to 1,000,000, and very particularly preferably 10 to 100,000.

The particles (in the following also in the general sense particulate inorganic matrix) according to the invention consist substantially (see also the definition of the structure types) of inorganic compounds, which are poorly soluble in water and physiological liquids, for example of topaz, $(Al_2F_2)[SiO_4]$, and chiolite, $Na[Al_3F_4]$, preferably wavellite, $Al_3(PO_4)_2(OH,F)_2$, calcium carbonate, $CaCO_3$, maghemite, $\gamma\text{-}Fe_2O_3$, particularly preferably zeolites, gen. formula $M_n[(AlO_2)_x(SiO_2)_y]$ (M=metal, e.g. Na), magnetite, $Fe_3O_4$, and barium sulphate, $BaSO_4$, and very particularly preferably gallium phosphate, $GaPO_4$, apatite or fluorohydroxyapatite, $Ca_5(PO_4)_3(OH,F)=3Ca_3(PO_4)_2*Ca(OH,F)_2$, and fluorspar, $CaF_2$.

The positron-emitting nuclides are preferably chosen from the group comprising $^{15}$O, [30]P, $^{13}$N, [65]Ga, [1,1]C, [131]Ba, [26]Al and $^{68}$Ga and [18]F. The medically, in particular diagnostically usable nuclides for the particles according to the invention are thus $^{15}$O, [30]P, $^{13}$N, preferably [65]Ga, $^{11}$C, particularly preferably [131]Ba, [26]Al, and very particularly preferably $^{68}$Ga or [18]F. All the medically usable isotopes known to the person skilled in the art can moreover be used to prepare particles according to the invention. An extract of some isotopes is to be found in Table 1.

TABLE 1

Extract of usable isotopes (incomplete selection)

| Isotope | Half-life | | Decay energy (MeV) | Spin parity | Decay type(s) or frequency (%) |
|---|---|---|---|---|---|
| 31S | 2.572 | s | 5.396 | 1/2+ | $K/\beta+ = 100$ |
| 15O | 122.24 | s | 2.754 | 1/2− | $K/\beta+ = 100$ |
| 30P | 2.498 | m | 4.232 | 1+ | $K/\beta+ = 100$ |
| 13N | 9.965 | m | 2.220 | 1/2− | $K/\beta+ = 100$ |
| 65Ga | 15.2 | m | 3.255 | 3/2− | $K/\beta+ = 100$ |
| 11C | 20.39 | m | 1.982 | 3/2− | $K/\beta+ = 100$ |
| 68Ga | 67.629 | m | 2.921 | 1+ | $K/\beta+ = 100$ |
| 18F | 109.77 | m | 1.656 | 1+ | $K/\beta+ = 100$ |
| 131Ba | 11.50 | d | | 1/2+ | $K/\beta+ = 100$ |
| 26Al | 7.17·105 | a | 4.004 | 5+ | $K/\beta+ = 100$ |
| $^{122}$Ba | 1.95 | m | | 0+ | $K/\beta^+ = 100$ |
| $^{123}$Ba | 2.7 | m | | 5/2+ | $K/\beta^+ = 100$ |
| $^{124}$Ba | 11.0 | m | | 0+ | $K/\beta^+ = 100$ |
| $^{125}$Ba | 3.5 | m | | 1/2(+) | $K/\beta^+ = 100$ |
| $^{126}$Ba | 100 | m | | 0+ | $K/\beta^+ = 100$ |
| $^{127}$Ba | 12.7 | m | | 1/2+ | $K/\beta^+ = 100$ |
| $^{129}$Ba | 2.23 | h | | 1/2+ | $K/\beta+ = 100$ |
| $^{129m1}$Ba | 2.16 | h | | 7/2+ | $K/\beta+ < 100$ |
| $^{131}$Ba | 11.50 | d | | 1/2+ | $K/\beta+ = 100$ |
| $^{51}$Fe | 305 | ms | 8.020 | 5/2− | $K/\beta^+ = 100$ |
| $^{52}$Fe | 8.275 | h | 2.372 | 0+ | $K/\beta^+ = 100$ |
| $^{52m1}$Fe | 45.9 | s | 9.192 | (12+) | $K/\beta^+ = 100$ |
| $^{53}$Fe | 8.51 | m | 3.743 | 7/2− | $K/\beta^+ = 100$ | s = seconds; m = minutes; d = days; a = years

The diameter of the particles according to the invention can be in a range of from 0.1 nm to 100 µm, preferably 1 nm to 10 µm, particularly preferably 1 nm to 1 µm.

In a preferred embodiment of the pharmaceutical agent according to the invention, the particles according to the invention are in a pharmaceutical shell.

According to the invention, the shell is chosen from the group comprising: a synthetic polymer or copolymer, a starch or a derivative thereof, a dextran or a derivative thereof, a cyclodextran or a derivative thereof, a fatty acid, a polysaccharide, a lecithin or a mono-, di- or triglyceride or a derivative thereof or mixtures thereof.

The synthetic polymer or copolymer can be chosen from the group comprising polyoxyethylene sorbitan esters, polyoxyethyls and derivatives thereof, polyoxypropyls and derivatives thereof, nonionic surface-active substances, polyoxystearates (35-80), polyvinyl alcohols, polymerized sucrose, polyhydroxyalkylmethacrylamides, lactic acid and glycollic acid copolymers, polyorthoesters, polyalkyl cyanoacrylates, polyethylene glycol, polypropylene glycol, polyglycerols, polyhydroxylated polyvinyl matrices, polyhydroxyethylaspartamides, polyamino acids, styrene and maleic acid copolymers, polycaprolactones, carboxypolysaccharides and polyanhydrides.

The starch derivative can be chosen from the group consisting of starch 2-hydroxymethyl ether and hydroxyethylstarch.

The dextran or derivative thereof can be chosen from the group comprising galactosylated dextran, lactosylated dextran, aminated dextran, dextran with SH groups, dextran with carboxyl groups, dextran with aldehyde groups and biotinylated dextran.

The cyclodextrin can be chosen from the group comprising beta-cyclodextrin and hydroxypropylcyclodextrin.

The fatty acid can be chosen from the group comprising sodium lauryl sulphate, sodium stearate, stearic acid, sorbitan monolaurate, sorbitan monooleates, sorbitan monopalmitate and sorbitan monostearate.

In another preferred embodiment of the pharmaceutical agent according to the invention, the inorganic particles are coupled to target-specific ligands. The ligand can be chosen from the group consisting of proteins, antibodies, antibody fragments, peptides, aptamers, darpins and other molecules which have a high affinity for disease-specific receptors. Appropriate molecules with receptor affinity are known to the person skilled in the art.

Three diagrammatized structure types or embodiments of the particles according to the invention are to be described here (see FIGS. 1 and 2):

DESCRIPTION OF FIGS. 1 AND 2

FIG. 1 Type 1 describes particles according to the invention from the group of poorly soluble inorganic compounds (C) described above, which are stabilizer-free and coagulation-inhibited. Adsorbed water molecules or/and the electric charge on the particle surface contribute towards stabilizing the particles here (systems also called sol).

FIG. 1 Type 2 are particles according to the invention which are stabilized against aggregation with surface-active molecules. In addition to the usual stabilizers which can be administered i.v., such as, for example, poloxamers, specially tailor-made block copolymers can also be employed. These include e.g. so-called double hydrophilic A-block-B copolymers, of which block A has coordinating/stabilizing abilities and the second block B protects the particles from aggregation and often consists of polyethylene glycol (PEG).

The particles according to the invention can moreover be coated with further materials, e.g. with conventional coating materials, such as carbohydrates, polyethylene glycols, polyacrylic or -methacrylic acids, fatty acids, silica or/and silane etc.

FIG. 1 Type 3 shows a further embodiment of the particles according to the invention with a target-specific particle structure, which are obtained by additional coupling of specific ligands. These ligands can be, for example, antibodies, fragments thereof, peptides, aptamers, darpins or other small molecules which have a high affinity for disease-specific receptors. The ligands can be either coupled via chemical modification of the substances used for the stabilization or anchored directly on the particle according to the invention.

In addition, the core of the particles according to the invention can consist of two different materials (core-shell structure; FIG. 2 Type 1.1, 1.2, 1.3). In this context, in a preferred embodiment the inner C2 (or outer C1) can consist of a further diagnostically usable agent. For example, magnetites (such as Resovist or Supravist, Schering AG Germany) can be used as nucleation seeds and the poorly soluble inorganic compounds described above can be precipitated on or applied to these.

In a further embodiment, the shell of the particles according to the invention of type 1.1, 1.2 and 1.3 can consist of any pharmaceutically acceptable shell.

The subject matter of the present invention is likewise a pharmaceutically usable composition in which at least 0.001% of the particles contained in the composition are the particles according to the invention. That is to say, under certain circumstances a low content of the particles contained in the pharmaceutical agent according to the invention in a pharmaceutically usable composition is already sufficient to make this composition diagnostically or therapeutically usable.

If the particles according to the invention are compared with FDG, the prior art of the PET tracer market, a number of advantages which can be derived directly from the particulate character of the particles according to the invention can be described.

1. Simple preparation: For preparation of the inorganic nanoparticles, in contrast to FDG no organic synthesis steps and purification are required. The inorganic particulate PET tracers according to the invention form spontaneously at room temperature. For example, this is effected by addition of the isotope, e.g. [18]F, to hydroxyapatite and mixing of the educts preformulated in the so-called "cold kit". The distribution centre or the nuclear medicine practitioner thus saves resources.

"Cold kit" here means that the particulate inorganic matrix is initially free from radioactive particles. Radioactive ions are then introduced directly before the use of the pharmaceutical agent by addition of appropriate radioactive nuclides in ionic form, the radioactive ions occupying lattice spaces in the inorganic matrix in an exchange reaction without the superlattice structure of the inorganic matrix being disturbed by this means.

2. Short preparation time: The preparation time of a formulation of the particles according to the invention is lower by at least the factor 10 than the time required for synthesis and purification of FDG of the same activity, i.e. more active product arrives at the customer in the same delivery time. The preparation time of the nanoparticles is determined by the speed of precipitation of the inorganic matrix and is conventionally less than 5 min, preferably less than 1 min, more preferably less than 10 s. For example, calcium fluoride particles form spontaneously within one second after mixing of the aqueous solutions of calcium chloride and sodium fluoride according to a precipitation reaction equation.

3. Longer usability: The half-life of the isotopes, for example $^{18}$F, is indeed a natural constant (t½ approx. 110 min), but a particle according to the invention in a diagnostically usable formulation can contain up to several hundred thousand $^{18}$F atoms, depending on the particle size, which is controlled by the preparation process. This means that each pharmacologically active particle is also active in the PET imaging a hundred thousand times longer than a singly [18] F-labelled tracer. This is of commercial interest in particular if 1:1 conjugates of expensive biomolecules, such as antibodies and PET isotopes, are used. Cells labelled in this way can also be monitored in the organism for longer by means of PET imaging.

4. Passive targeting: Healthy blood vessels have a closed endothelium. They are impervious and hold larger molecules, such as e.g. albumin or also nanoparticles, back in the bloodstream. The endothelium of blood vessels in tumours has holes, and through these, small particles according to the invention can easily diffuse from the bloodstream into the tissue. Since moreover lymph transportation is reduced in tumour tissue, the particles according to the invention accumulate in the tumour—solely due to the correct nanoscale size.

5. Specificity: Nanoparticles are suitable for cell-associated targeting, i.e. the particles are chiefly taken up by cells of the RES, depending on their size and surface structure and charge. In this context, macrophages circulating in the blood can be labelled directly with particles according to the invention after injection of the formulation. This makes possible imaging of, for example, inflammatory processes, which are always accompanied by increased macrophage activity.

6. Platform for molecular imaging: In addition to the possibilities of passive and cell-associated targeting, the particles according to the invention offer a further targeted addressing of the inorganic particles. By coupling disease-specific ligands to the surface of the particles according to the invention, active targeting of receptors e.g. on cell surfaces is made possible.

7. Lower exposure to radiation in the brain: In contrast to FDG, prior art, particles according to the invention do not accumulate non-specifically in the brain. On the one hand this reduces the exposure of the brain to radiation, and on the other hand an investigation of neurological problems is possible.

8. Detection of very small foci: In addition to further factors, the spatial resolution of PET imaging depends intrinsically on the average free path length of the positrons in the tissue (for example approx. 3 mm in the case of positrons from $^{18}$F). Since, for example, an $^{18}$F isotope of FDG decays freely in tissue, the resolution cannot be brought below this physical limit. In contrast, the isotopes of the particles according to the invention are firmly enclosed in a crystal lattice. This increases the probability of interaction of the positrons with electrons and reduces the average free path length. An improvement in the PET spatial resolution can be achieved. A resolution with which tumours with a diameter of less than 3 mm can be detected is therefore possible. This resolution indeed cannot be achieved in every case, for it depends on the detector used, but is accessible with suitable detectors.

9. Extended spectrum of use: The particles according to the invention have a similar or even higher electron density in relation to bone, i.e. an accumulation of particles can be imaged directly in the CT. A non-radioactive formulation of particles according to the invention (for example consisting of $CaF_2$, the naturally most frequent fluorine isotope, $^{19}$F, is not radioactive) is suitable for imaging in F-MRI.

10. Multimodal imaging: Particles according to the invention, in particular of embodiment 1.1, 1.2 and 1.3 (see FIG. 2) are suitable for multimodal imaging, since these contain a further diagnostically usable substance in addition to the positron emitter.

Possible Preparation Variants

The invention moreover relates to methods for the preparation of pharmaceutical agents containing a particulate inorganic matrix, which in addition to the natural isotope distribution of the structure type-forming elements of the anions and cations, contains contents of positron-emitting nuclides, wherein the number of positron-emitting nuclides per particulate inorganic matrix is preferably greater than or equal to 1.

The subject matter of the present invention is thus also a method for the preparation of a pharmaceutical agent according to the invention comprising at least one of the following steps:

(i) Mixing of at least two solutions of soluble salts according to a precipitation reaction equation, wherein at least one salt is enriched with positron-emitting nuclides and wherein the cations of the one salt precipitate out with the anions of the other salt and wherein the positron-emitting content is part of the precipitated compound, and a particulate inorganic matrix forms which, in addition to the natural isotope distribution of the structure type-forming elements of the anions and cations, contains contents of positron-emitting nuclides.

(ii) Formation of a suspension according to a precipitation reaction equation containing the particulate inorganic matrix which, in addition to the natural isotope distribution of the structure type-forming elements of the anions and cations, contains contents of positron-emitting nuclides.

(iii) Mixing of at least two solutions of soluble salts according to a precipitation reaction equation to form an inorganic matrix and subsequent addition of the positron-emitting nuclides in anionic or cationic form.

Furthermore, the subject of the present invention is also a method for the preparation of a pharmaceutical agent according to the invention comprising at least one of the following steps:

(iv) Mixing of at least two solutions of soluble salts according to a precipitation reaction equation, wherein at least one salt is enriched with at least one of the abovementioned positron-emitting nuclides and wherein the cations of the one salt precipitate out with the anions of the other salt and wherein the positron-emitting content is part of the precipitated compound, and a particulate inorganic matrix forms which, in addition to the natural isotope distribution of the structure type-forming elements of the anions and cations, contains contents of at least one of the abovementioned positron-emitting nuclides.

(v) Formation of a suspension according to a precipitation reaction equation containing the particulate inorganic matrix which, in addition to the natural isotope distribution of the structure type-forming elements of the anions and cations, contains contents of at least one of the abovementioned positron-emitting nuclides.

(vi) Mixing of at least two solutions of soluble salts according to a precipitation reaction equation to form an inorganic matrix and subsequent addition of at least one of the abovementioned positron-emitting nuclides in anionic or cationic form.

In the context of the present invention, stabilizers and/or ligand-carrying stabilizers can be added. In the context of the present invention, non-radioactive isotopes can additionally be used. The preparation and use of precursors as nucleation seeds for the method according to the invention can optionally be carried out. The method according to the invention can likewise be carried out by using exchange processes, which make possible, for example, an exchange of OH$^-$ ions for [18]F$^-$ ions in the particle structure. In the method according to the invention, the particle size can be controlled by varying the concentration ratios of the educts (starting substances). The method according to the invention can be followed by steps for modification of the surface properties by choice of the pharmaceutical shell. The method can be followed by steps for coupling ligands by physical and chemical as well as biochemical methods known to the person skilled in the art. In the method according to the invention, the isotonicity of the formulation can be adjusted. In the method according to the invention, sterilization, autoclaving or sterile filtration can optionally be carried out. In the method according to the invention, inorganic particles of a predetermined total particle diameter can be selected in a further step.

Preferred embodiments of the method according to the invention are described in more detail in the following.

(a) General Preparation:

The compounds described above can be prepared by simple mixing of two aqueous solutions of the water-soluble salts with natural isotope distribution and the required amount of positron-emitting educts. This can be carried out, for example, by dropwise addition, with stirring or shaking, in special mixing chambers, e.g. three-way flow mixers (in the form of an Y) with two inlet lines, a mixing chamber and a discharge line, or also by using micromixers, which are known from microsystems technology. The usual modules for special synthesis of radiopharmaceuticals can also be used, since these contain the necessary mixing and stirring elements in their construction. However, the preparation of the particles described here is so simple that a convenient mixing system in which educts, mixing chamber and application injector are combined can also be developed. The particulate suspension forms immediately after mixing of the solutions and the preparation time is in the range of seconds.

(b) Optional Preparation of Various Structure Types:

The mixing can be carried out without the addition of stabilizer (structure type 1 and 1.1; FIGS. 1 and 2), with stabilizer (structure type 2 and 2.1; FIGS. 1 and 2) or with ligand-carrying stabilizer (structure type 3 and 3.1; FIGS. 1 and 2). A coprecipitation with ligands or modified ligands can also be carried out.

(c) Optional Additional Use of Non-Radioactive Isotopes:

The particles can be prepared from the soluble compounds directly with the radioactive isotopes, for example [18]F$^-$, which is obtained in aqueous solution by a nuclear reaction in a cyclotron. The process procedure can be optimized by using non-radioactive isotopes, such as e.g. [19]F$^-$.

(d) Optional Preparation and Use of Precursors:

A further preparation variant lies in the use of precursors, which can serve as nucleation seeds, so that a core-shell structure forms. The target compound itself—although with the natural isotope distribution—or also a second contrast medium, such as e.g. magnetite or maghemite particles, can be employed as the nucleation seed.

(e) Optional Preparation Using Exchange Processes:

Non-radioactive nuclides in an inorganic matrix can be subsequently exchanged by radioactive nuclides in the context of the present invention, in order thus to produce the inorganic matrix according to the invention. By the example of hydroxyapatite, a finished formulation of the structure types according to the invention can be reacted quite simply with aqueous [18]F$^-$ solution. The [18]F$^-$ ions replace OH$^-$ ions in the hydroxyapatite structure and particulate $^{18}$F-fluorohydroxyapatite, $Ca_5(PO_4)_3(OH, [18]F)$, is formed without the superlattice structure being disturbed.

(f) Optional Control of the Particle Size:

The size of the nanoparticles can be controlled by the concentration ratios of the educts (starting substances).

In the method according to the present invention, the ions employed in the precipitation reaction which make up the inorganic matrix are preferably added in a concentration of from $1*10^{-11}$ mol/l to 40 mol/l, more preferably in a concentration of from $1*10^{-7}$ mol/l to 10 mol/l, most preferably $1*10^{-4}$ mol/l to 1 mol/l. By establishing certain concentrations of the ions in the precipitation reaction, the desired size of the particles according to the invention can be adjusted, as stated above.

Particularly preferably, in the method according to the present invention the ions employed in the precipitation reaction which make up the inorganic matrix are added in a concentration of from $1.1*10^{-4}$ to 184 g/l in the case of topaz $(Al_2F_2)[SiO_4]$ as the inorganic matrix, in a concentration of from $3.9*10^{-4}$ to 180 g/l in the case of chiolite $Na[Al_3F_4]$ as the inorganic matrix, in a concentration of from $2.1*10^{-4}$ to 343 g/l in the case of wavellite $Al_3(PO_4)_2(OH,F)_2$ as the inorganic matrix, in a concentration of from $7.1*10^{-3}$ to 100 g/l in the case of calcium carbonate $(CaCO_3)$ as the inorganic matrix, in a concentration of from $9.4*10^{-4}$ to 160 g/l in the case of maghemite $(\gamma-Fe_2O_3)$ as the inorganic matrix, in a concentration of from $1.3*10^{-4}$ to 230 g/l in the case of zeolites (gen. formula $M_n[(AlO_2)_x(SiO_2)_y]$ (M=metal, e.g. Na)) as the inorganic matrix, in a concentration of from $9.4*10^{-4}$ to 230 g/l in the case of magnetite $(Fe_3O_4)$ as the inorganic matrix, in a concentration of from $9.1*10^{-3}$ to 233 g/l in the case of barium sulphate $(BaSO_4)$ as the inorganic matrix, in a concentration of from $5.2*10^{-9}$ to 164 g/l in the case of gallium phosphate $(GaPO_4)$ as the inorganic matrix, in a concentration of from $1.8*10^{-4}$ to 504 g/l in the case of apatite or fluorohydroxyapatite $(Ca_5(PO_4)_3(OH,F)=3Ca_3(PO_4)_2*Ca(OH,F)_2)$ as the inorganic matrix and in a concentration of from $1.6*10^{-2}$ to 78 g/l in the case of fluorspar $(CaF_2)$ as the inorganic matrix.

In the method according to the present invention, the precipitation reactions are preferably carried out at a temperature of from 0° C. to 100° C., more preferably at 4° C. to 60° C., most preferably at 10° C. to 40° C.

(g) Optional Modification of the Surface Properties:

By using different stabilizers, the surface properties can be determined. Those stabilizers which form a pharmaceutical shell are preferred.

(h) Optional Coupling of Ligands:

The addition of ligands by the usual physical and chemical as well as biochemical methods. Appropriate coupling methods are known to the person skilled in the art.

(i) Optional Adjusting Isotonicity:

By the use of the particular soluble Cl or Na compounds—or other conventional substances for isotonicizing—the later isotonicity of the resulting formulation can be taken into account directly. An isotonic solution has the same osmotic pressure as human blood (about 7.5 bar) and corresponds to a saline solution with a concentration of about 0.9%.

(j) Optional Sterilization/Autoclaving/Sterile Filtration:

The formulations—precursor or finished preparation—can be sterilized by conventional methods. Suitable methods are, inter alia, sterile filtration with a pore size of 0.2 µm or heat sterilization in an autoclave at 121° C., 1 bar, 15 to 30 min.

The embodiments and preparation methods described demonstrate that the particles according to the invention can be provided in various formulations with respect to their properties, such as, for example, composition, isotope content, size and surface properties, which can thus be matched to the pharmacological requirements in a targeted manner.

Use of the Particles According to the Invention

The pharmaceutical agents according to the invention are employed in vitro and in vivo in medicine, preferably as diagnostic agents. Use in positron emission tomography (PET) and also PET-CT image-assisted diagnosis is particularly preferred. The particles according to the invention can be employed both in pharmacological research and in veterinary medicine and also in human medicine. For diagnostic uses, the active dose is administered to a patient. The administration is preferably intravenous. The distribution of the particles according to the invention in the body is then determined by PET or PET-CT or optionally by other suitable methods after predetermined times. Appropriate methods are known to the person skilled in the art. The pharmaceutical agents according to the invention are likewise employed in locoregional therapy.

Possible indications and use mechanisms are described in the following by way of example.

Use of the Particles According to the Invention Analogously to Colloids for MRI, e.g. Resovist and Supravist (Schering AG, Germany)

The use of the particles according to the invention in all Resovist indications, e.g. investigation of the liver, and Supravist indications, e.g. angiography, is possible.

Use of the Particles According to the Invention Analogously to Colloids for SPECT, e.g. NanoCis (CisBio, France)

The use of the particles according to the invention in all NanoCis/NanoColl indications, e.g. sentinel lymph node detections, is possible in principle. The core-shell structure types with magnetite in the core can also be used for combined imaging methods in the field of sentinel lymph node detection.

Use of the Particles According to the Invention for "Passive Targeting"

Controlling the size and surface properties allows nanoparticles to be tailor-made for passive targeting of tumour tissue. The mechanism of passive targeting is shown schematically in FIG. 3.

DESCRIPTION OF FIG. 3

Healthy blood vessels have a closed endothelium. They are impervious and hold larger molecules, such as e.g. albumin or also nanoparticles, back in the bloodstream. The endothelium of blood vessels in tumours has holes, and through these, small particles according to the invention can easily diffuse from the bloodstream into the tissue. Since moreover lymph transportation is reduced in tumour tissue, the particles according to the invention accumulate in the tumour—solely due to the correct nanoscale size.

The specific medium in tumour tissue can moreover ensure that the particles according to the invention assume other diagnostically usable properties there.

Use of the Particles According to the Invention for Cell-Associated Targeting

The particles according to the invention are chiefly taken up by cells of the RES, depending on size and surface structure and charge. In this context, macrophages circulating in the blood can be labelled directly with particles according to the invention after injection of the formulation. This makes possible imaging of, for example, inflammatory processes, which are always accompanied by increased macrophage activity.

Use of the Particles According to the Invention for "Active Targeting"

With the aid of specific ligands, tissue structures can be recognized in a targeted manner. For example, anti-L-selectin is suitable for demonstrating lymph nodes. ICAM and VCAM are specific inflammation markers, which also play a major role in the case of detection of MS. E-selectin is moreover suitable for recognition of inflammation foci and also many types of tumour. EDB-fibronectin is angiogenesis-specific and an anti-CD105 (endoglin) antibody can be used for demonstration of breast cancer. Further ligands and receptors which can be used are known to the person skilled in the art.

Since the preparation of the particles according to the invention is uncomplicated, and specific ligands can be changed in particular via the stabilizers, the particles according to the invention serve as a flexible platform technology.

Use of the Particles According to the Invention for Stem Cell Imaging (Stem Cell Tracking)

Stem cell markings are possible with the particles according to the invention.

Use of the Particles According to the Invention for Overcoming the Blood/Brain Barrier (BBB Delivery)

With the aid of delivery strategies known from the literature (e.g. pathfinder technology), it is possible to cross the blood/brain barrier.

Thus, the subject matter of the present invention is also a pharmaceutical agent according to the invention for diagnosis by means of positron emission tomography of a disease chosen from the group consisting of proliferative diseases, inflammatory diseases, autoimmune diseases, diseases of the digestive tract, arteriosclerosis, stroke, infarction, pathological changes to the blood vessel system, the lymph system, the pancreas, the liver, the kidney, the brain and the bladder, and diseases of electric stimulus transmission and neurodegenerative diseases. In this context, the proliferative disease can be chosen from the group consisting of a tumour, a precancerous stage, a dysplasia, an endometriosis and a metaplasia. In this context, the autoimmune disease can be chosen from the group consisting of rheumatoid arthritis, inflammatory intestinal disease, osteoarthritis, neuropathic pain, alopecia areta, psoriasis, psoriatic arthritis, acute pancreatitis, allograft rejection, allergies, allergic inflammations of the lung, multiple sclerosis, Alzheimer's, Crohn's disease and systemic lupus erythematosus.

Thus, the subject matter of the present invention is also a pharmaceutical agent according to the invention for locoregional therapy of a disease chosen from the group comprising proliferative diseases, inflammatory diseases, autoimmune diseases, diseases of the digestive tract, arteriosclerosis, stroke, infarction, pathological changes to the blood vessel system, the lymph system, the pancreas, the liver, the kidney, the brain and the bladder, and diseases of electric stimulus transmission and neurodegenerative diseases. In this context, the proliferative disease can be chosen from the group consisting of a tumour, a precancerous stage, a dysplasia, an endometriosis and a metaplasia. In this context, the autoimmune disease can be chosen from the group consisting of rheumatoid arthritis, inflammatory intestinal disease, osteoarthritis, neuropathic pain, alopecia areta, psoriasis, psoriatic arthritis, acute pancreatitis, allograft rejection, allergies, allergic inflammations of the lung, multiple sclerosis, Alzheimer's, Crohn's disease and systemic lupus erythematosus.

The invention is furthermore explained by the following examples:

DETAILED EXAMPLE 1

Nanoparticulate Calcium Fluoride, $CaF_2$, as a PET Diagnostic Agent

1.1 General Description $CaF_2$ precipitates as a poorly soluble compound (solubility of fluorspar: 17 mg/l at 20° C. and 16 mg/l at 18° C.) as a sediment after mixing of the water-soluble compounds $CaCl_2$ and NaF (a successful preparation can also be carried out with KF, $NH_4F$ or HF) or also in colloidally dispersed form ("nanoparticles") after mixing of suitable low concentration ratios.

Precipitation Reaction Equation:

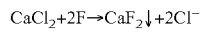

$$CaCl_2 + 2F^- \rightarrow CaF_2\downarrow + 2Cl^-$$

In the presence of suitable stabilizers, for example poloxamer F68, nanoparticles are also formed on mixing of far higher concentration ratios. Calcophilic stabilizers, such as block copolymers of the polyacrylic acid-block-PEG, phosphate-functionalized polymers-block-PEG and phosphonate-functionalized polymers-block-PEG type, are particularly suitable for this.

This can be deduced with the aid of the "low molecular" solubility products:

| | |
|---|---|
| Ca carboxylate | pKs (25° C.) = 8.1 |
| Ca phosphate | pKs (25° C.) = 29.5 |
| Ca phosphonate | pKs (25° C.) = 52 |

Chemical coupling of the stabilizers to target-specific ligands, such as antibodies, fragments thereof, peptides etc. of the ligand-PEG-block-calcophilic polymer type gives nanoparticles which can bond in a targeted manner to corresponding targets in the patient.

$[18]F^-$ behaves chemically like $[19]F^-$. For a PET diagnostic agent, $[18]F^-$, for example as H[18]F or Na[18]F solution, of the required radioactivity is added to the Na[19]F solution, the components are mixed and the product is employed for precipitation according to the precipitation reaction.

The nuclide $^{18}$F has a half-life of approx. $t\frac{1}{2} = 110$ min. It is prepared according to the following target reaction in a cyclotron:

| Target material | Target reaction | Product | Nuclide |
|---|---|---|---|
| [18]O—$H_2O$ | ... [18]O → (p, n) → [18]F ... | $[18]F^-$ | [18]F |

$[18]F^-$ is obtained as HF in aqueous solution. The fluoride concentration here is as a rule between 50 and 400 GBq/μmol, depending on the process procedure and the model of the cyclotron.

1.2 Procedure

1.2.1 Surfactant-Free $CaF_2$ Nanoparticles

The appropriate amount of $[18]F^-$ solution is mixed with non-radioactive potassium fluoride (KF) solution so that 1 ml of an aqueous KF solution of concentration 0.1 mol/l is formed. 1 ml of the aqueous KF solution (0.1 mol/l) are mixed, by shaking in a vial, with 1 ml of an aqueous $CaCl_2$ solution of concentration 0.05 mol/l. The $CaF_2$ nanoparticles form immediately, which can be seen from the slight opalescence of the dispersion formed (FIG. 4).

The determination of the particle size distribution by dynamic light scattering (DLS) gives an average particle size of 71.5 nm (intensity-weighted).

The repetition of the experiment gives a particle size of 81.7 nm.

With the aid of thin layer chromatography (mobile phase: methanol or methyl ethyl ketone) and a suitable detector, it can be demonstrated that more than 90% of the radioactivity employed is bonded in the particles according to the invention and remains on the base line (Rf=0).

In a second series of experiments, instead of the KF solution a sodium fluoride (NaF) solution (0.1 mol/l) is mixed with 1 ml of an aqueous $CaCl_2$ solution (0.05 mol/l). Here also $CaF_2$ nanoparticles are formed and the dispersion looks opalescent. The particle size determination by DLS gives 75.9 nm here. Here also more than 90% of the radioactivity employed is bonded in the particles according to the invention.

1.2.2 Surfactant-Stabilized $CaF_2$ Nanoparticles 1 ml of an aqueous KF solution (0.1 mol/l) with the desired radioactivity are mixed, by shaking in a vial, with 1 ml of an aqueous $CaCl_2$ solution (0.05 mol/l), in which 1 wt. % of Pluronic F68 (also known as poloxamer 188) was dissolved beforehand. The $CaF_2$ nanoparticles form immediately, which can be seen by the slight opalescence of the dispersion formed.

More than 90% of the radioactivity employed is bonded in the particles according to the invention.

The determination of the particle size distribution by dynamic light scattering gives an average particle size of 64.5 nm (intensity-weighted). An example of a particle size distribution is shown in FIG. 5.

The experiment is repeated seven times and the particle size determined by DLS. After 24 h the particle size distribution is measured again. The results are summarized in Table 2.

TABLE 2

Average particle size of F68-stabilized $CaF_2$ nanoparticles directly after preparation and 24 hours later.

| Sample | Intensity-weighted [nm] | Stability [24 h] |
|---|---|---|
| 1 | 64.5 | 66.7 |
| 2 | 64.6 | 66.1 |
| 3 | 61.3 | 64.0 |
| 4 | 57.1 | 60.4 |
| 5 | 59.4 | 70.8 |
| 6 | 54.8 | 61.5 |
| 7 | 57.3 | not determined |
| mean [nm] | 60.3 | 64.9 |
| st. dev. [nm] | 4.0 | 3.5 |
| VC [%] | 6.6 | 5.3 |

The series of experiments shows a very good reproducibility of the nanoparticle size (variation coefficient<7%). The mean particle size after a standing time of 24 hours at room temperature increases slightly from 60.3±4.0 nm (n=7) to 64.9±3.5 nm (n=6), but this increase is still within the framework of the simple standard deviation of the series of experiments and is therefore statistically not significant. Therefore, the $CaF_2$ nanoparticles are stable with respect to the particle size distribution for at least 24 h.

1.2.3 Controlling the Particle Size of the $CaF_2$ Nanoparticles

Analogously to the series of experiments described above, $CaF_2$ nanoparticles are prepared from more highly concentrated KF solution and $CaCl_2$ solution. Together with the results on testing of the reproducibility (Example 1.2.2), the particle sizes as a result of mixing of in each case 1 ml of 0.2 mol/l KF solution with 0.1 mol/l CaCl$_2$ solution or 0.4 mol/l KF solution with 0.2 mol/l CaCl$_2$ solution are shown in FIG. 6. The particle size increases from about 60 nm up to about 400 nm with increasing concentration.

Example 2

Nanoparticulate Poorly Soluble Inorganic $^{11}$C or [15]O Carbonate Compound and the Use Thereof as a PET Diagnostic Agent Example Nanoparticulate Calcium Carbonate, CaCO$_3$, as a PET Diagnostic Agent The nuclides are prepared by the following target reaction in a cyclotron:

| Target material | Target reaction | Product | Nuclide |
|---|---|---|---|
| N$_2$ + 0.5% O$_2$ | ... N14 → (p, α) → C11 ... | CO$_2$ | [11]C |
| N$_2$ + 2% O$_2$ | ... N14 → (d, n) → C15 ... | CO$_2$ | [15]C |

C[11] t½ = 20.7 min
O[15] t½ = 2 min

Precipitation Reaction Equation:

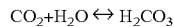

$$CO_2 + H_2O \leftrightarrow H_2CO_3$$

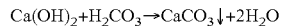

$$Ca(OH)_2 + H_2CO_3 \rightarrow CaCO_3 \downarrow + 2H_2O$$

Nanoparticles are formed according to the precipitation reaction in the presence of suitable stabilizers, for example F68. Calcophilic stabilizers, such as block copolymers of the polyacrylic acid-block-PEG, phosphate-functionalized polymers-block-PEG and phosphonate-functionalized polymers-block-PEG type, are particularly suited. Chemical coupling of the stabilizers to target-specific ligands, such as antibodies, antibody fragments, peptides etc. of the ligand-PEG-block-calcophilic polymer type gives nanoparticles, which can bond in a targeted manner to corresponding targets in the patient.

Example 3

Nanoparticulate [18]Fluorohydroxyapatite Compounds (Ca$_5$(PO$_4$)$_3$(OH, $^{18}$F) and the Use Thereof as a PET Diagnostic Agent 3.1. Preparation of the Hydroxyapatite Particles Citric acid is added to a 0.1 molar aqueous CaCl$_2$ solution so that it is present in a concentration of 5 percent by weight. A pH of 9-11 is established with 0.1 molar NaOH solution. An aqueous Na$_3$PO$_4$ is then prepared in a manner such that a Ca/P ratio of 1.67 results in the solutions. The Na$_3$PO$_4$ solution is added dropwise to the CaCl$_2$ solution at room temperature, while stirring with a magnetic stirrer. A precipitate of hydroxyapatite forms.

3.2. Preparation of the [18]Fluorohydroxyapatite Particles

For preparation of the [18]fluorohydroxyapatite particles, a dispersion according to Example 3.1. is mixed with a solution containing [18]F$^-$ ions in the required radioactivity intensity, that is to say in the appropriate concentration. By exchanging hydroxyl ions for fluoride ions, [18]fluorohydroxyapatite particles suitable for diagnostic imaging are formed.

BRIEF DESCRIPTION OF THE DRAWINGS

FIG. 1 Type 1 describes particles according to the invention from the group of poorly soluble inorganic compounds (C) described above, which are stabilizer-free and coagulation-inhibited. Adsorbed water molecules or/and the electric charge on the particle surface contribute towards stabilizing the particles here (systems also called sol).
FIG. 1 Type 2 are particles according to the invention which are stabilized against aggregation with surface-active molecules. In addition to the usual stabilizers which can be administered i.v., such as, for example, poloxamers, specially tailor-made block copolymers can also be employed. These include e.g. so-called double hydrophilic A-block-B copolymers, of which block A has coordinating/stabilizing abilities and the second block B protects the particles from aggregation and often consists of polyethylene glycol (PEG).
The particles according to the invention can moreover be coated with further materials, e.g. with conventional coating materials, such as carbohydrates, polyethylene glycols, polyacrylic or -methacrylic acids, fatty acids, silica or/and silane etc.
FIG. 1 Type 3 shows a further embodiment of the particles according to the invention with a target-specific particle structure, which are obtained by additional coupling of specific ligands. These ligands can be, for example, antibodies, fragments thereof, peptides, aptamers, darpins or other small molecules which have a high affinity for disease-specific receptors. The ligands can be either coupled via chemical modification of the substances used for the stabilization or anchored directly on the particle according to the invention.
FIG. 2: In addition, the core of the particles according to the invention can consist of two different materials (core-shell structure;
FIG. 2 Type 1.1, 1.2, 1.3). In this context, in a preferred embodiment the inner C2 (or outer C1) can consist of a further diagnostically usable agent. For example, magnetites can be used as nucleation seeds and the poorly soluble inorganic compounds described above can be precipitated on or applied to these.
In a further embodiment, the shell of the particles according to the invention of type 1.1, 1.2 and 1.3 can consist of any pharmaceutically acceptable shell.
FIG. 3: Illustration of the mechanism of passive targeting. Healthy blood vessels have a closed endothelium. They are impervious and hold larger molecules, such as e.g. albumin or also nanoparticles, back in the bloodstream. The endothelium of blood vessels in tumours has holes, and through these, small particles according to the invention can easily diffuse from the bloodstream into the tissue. Since moreover lymph transportation is reduced in tumour tissue, the particles according to the invention accumulate in the tumour—solely due to the correct nanoscale size.

FIG. 4: Photograph of a $CaF_2$ dispersion according to Example 1.2.1 ready for administration. The $CaF_2$ nanoparticles are to be seen by the slight opalescence of the dispersion formed.

FIG. 5: Example of a particle size distribution of $CaF_2$ nanoparticles according to Example 1.2.2 determined by dynamic light scattering.

FIG. 6: Controlling the particle size of the $CaF_2$ nanoparticles with the aid of 11 independent experiments analogously to the preparation instructions described according to Example 1, in particular according to Example 1.2.3. The average diameter of the particle size distribution can be adjusted in this way from 60 nm to about 400 nm.

Figure 1:
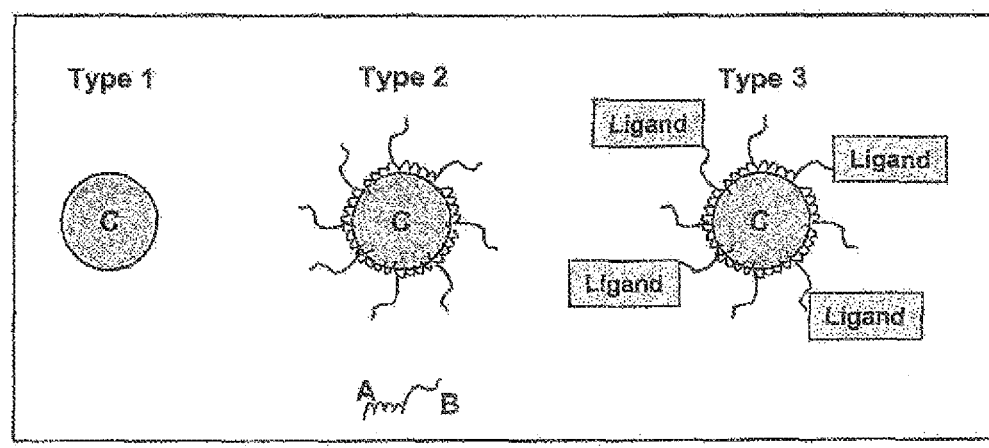
FIG. 1 illustrates 3 types of embodiments of particles.
Figure 2:
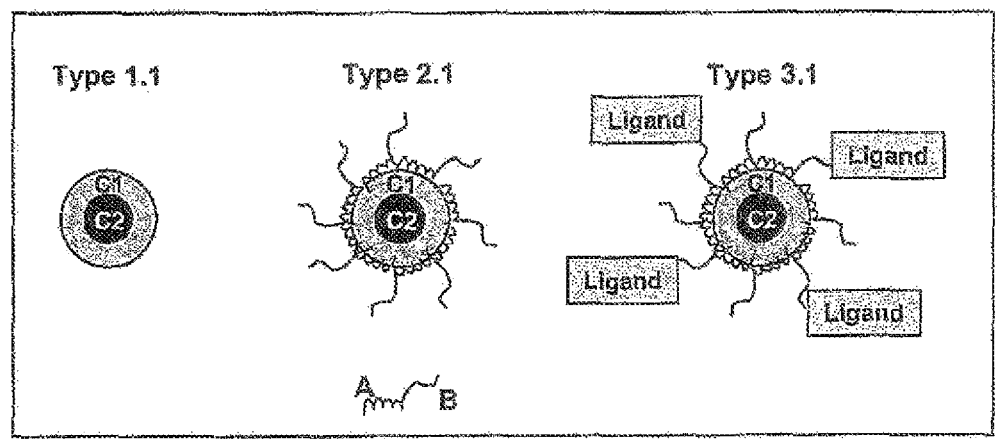
FIG. 2 illustrates 3 types of embodiments of particles.
Figure 3:
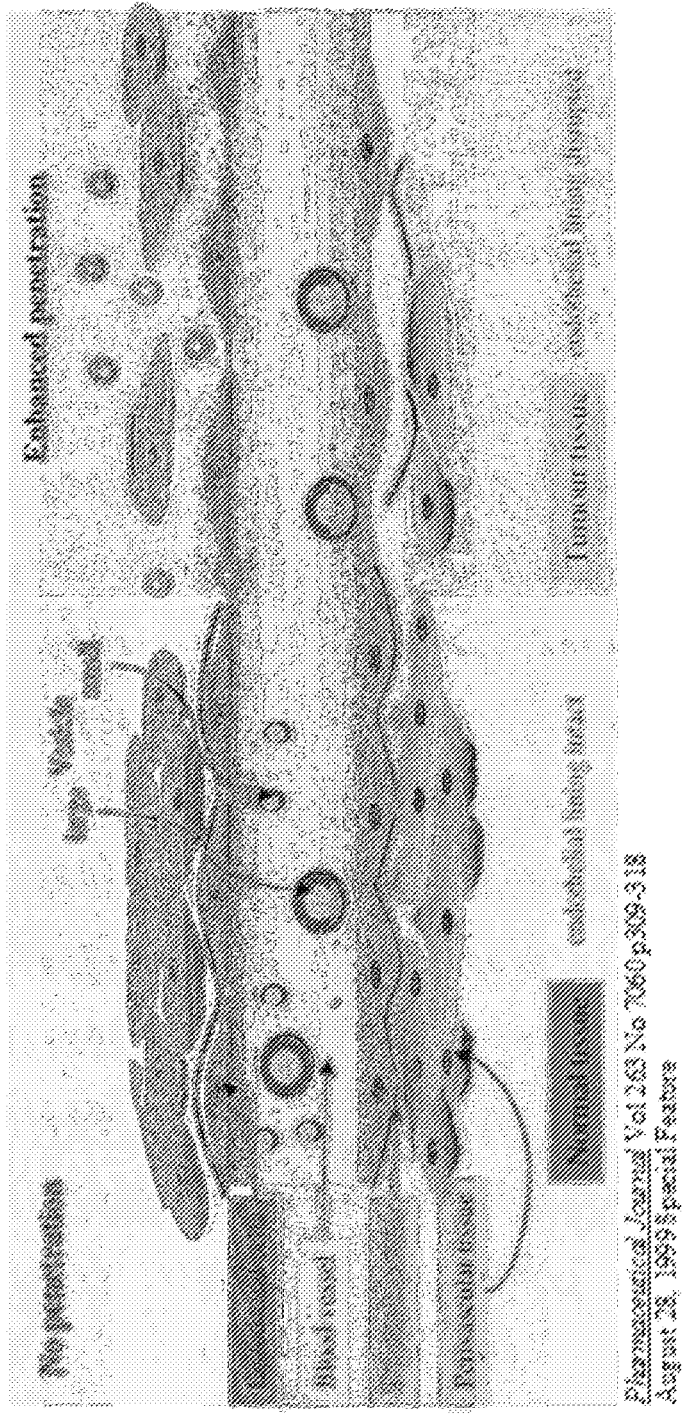
FIG. 3 illustrates mechanism of passive targeting.
Figure 4:
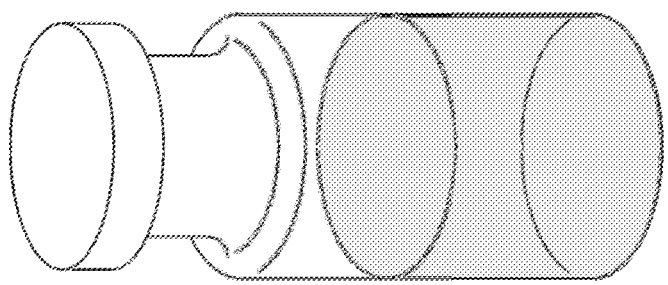
FIG. 4 illustrates a converted drawing from a photograph of a CaF$_2$ dispersion. The CaF$_2$ nanoparticles are to be seen by the slight opalescence of the dispersion formed, i.e., a dispersion of nanoparticles is apparent from the opaque shimmering light of the opalescent liquid, which is in contrast to a mere solution without nanoparticles, which would appear clear and transparent.
Figure 5:
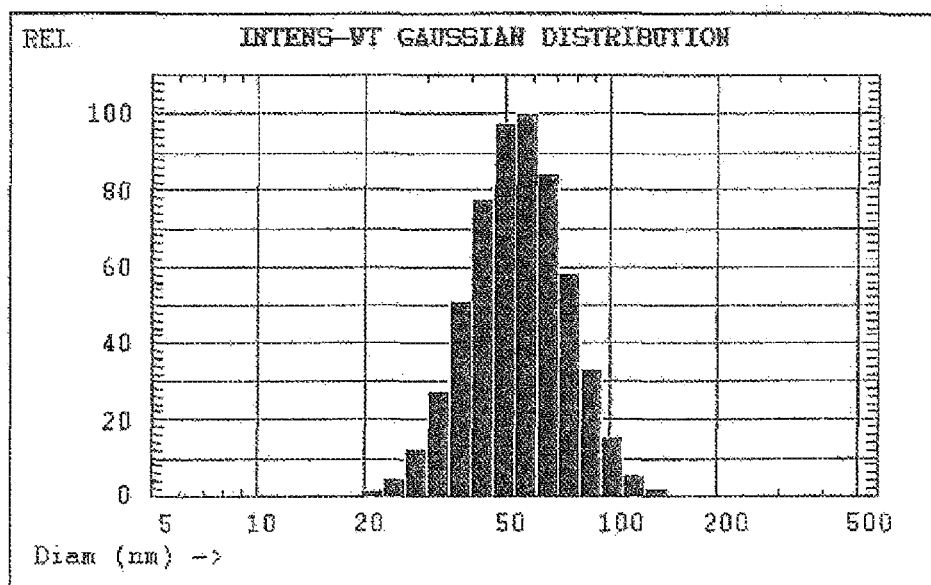
FIG. 5 illustrates an example of a particle size distribution of CaF$_2$ nanoparticles.
Figure 6:
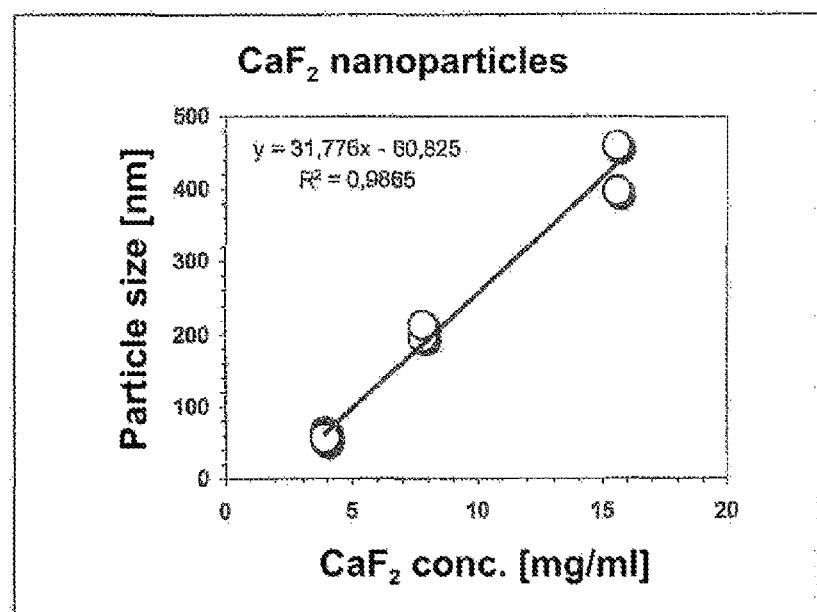
FIG. 6 illustrates a graph of CaF$_2$ concentration versus particle size.

The invention claimed is:

1. A pharmaceutical agent containing a particulate inorganic matrix, which in addition to the natural isotope distribution of the structure type-forming elements of anions or cations, contains contents of positron-emitting nuclides, wherein at least some of the positron-emitting nucleotides form part of the matrix,
wherein the structure type forming elements comprise amorphous structures or a mixture of amorphous structures and crystal structures,
wherein the number of positron-emitting nuclides per particulate inorganic matrix is greater than or equal to 1, wherein the particulate inorganic matrix is selected from the group consisting of topaz $(Al_2F_2)[SiO_4]$, chiolite $Na[Al_3F_4]$, wavellite $Al_3(PO_4)_2(OH,F)_2$, calcium carbonate $(CaCO_3)$, maghemite $(\gamma-Fe_2O_3)$, zeolites, magnetite $(Fe_3O_4)$, barium sulphate $(BaSO_4)$, gallium phosphate $(GaPO_4)$, apatite or fluorohydroxyapatite $(Ca_5(PO_4)_3(OH,F)=3Ca_3(PO_4)_2*Ca(OH,F)_2)$ and fluorspar $(CaF_2)$, wherein the particulate inorganic matrix is coupled to a target-specific ligand and
wherein the positron-emitting nuclides are selected from the group consisting of $^{15}$O, [30]P, $^{13}$N, [65]Ga, $^{11}$C, [131]Ba, [26]Al, $^{68}$Ga and [18]F.

2. The pharmaceutical agent according to claim 1, wherein the particulate inorganic matrix has a diameter of 0.1 nm to 100 μm.

3. The pharmaceutical agent according to claim 1, wherein the particulate inorganic matrix is in a pharmaceutical coating.

4. A pharmaceutical composition, comprising a pharmaceutically acceptable carrier and the pharmaceutical agent according to claim 1, wherein at least 0.001% of particles contained in the composition are particulate inorganic matrices of said pharmaceutical agent.

5. A method for diagnostic imaging, comprising performing said imaging with a pharmaceutical agent according to claim 1.

6. A method for locoregional therapy of a disease, comprising administering to a subject in need thereof an effective amount of a pharmaceutical agent according to claim 1.

7. The pharmaceutical agent according to claim 1, wherein the structure type forming elements comprise only amorphous structures.

8. The pharmaceutical agent according to claim 1, wherein the structure type forming elements comprise a mixture of amorphous structures and crystal structures.

9. The pharmaceutical agent according to claim 1, wherein the zeolites have are of formula $M_n[(AlO_2)_x(SiO_2)_y]$, wherein M is a metal, n is the number of metal groups, x is the number of $AlO_2$ groups, and y is the number of $SiO_2$ groups.

10. The pharmaceutical agent according to claim 1, wherein the positron-emitting nuclides are [15]O.

11. The pharmaceutical agent according to claim 1, wherein the positron-emitting nuclides are [30]P.

12. The pharmaceutical agent according to claim 1, wherein the positron-emitting nuclides are [13]N.

13. The pharmaceutical agent according to claim 1, wherein the positron-emitting nuclides are [65]Ga.

14. The pharmaceutical agent according to claim 1, wherein the positron-emitting nuclides are [11]C.

15. The pharmaceutical agent according to claim 1, wherein the positron-emitting nuclides are [131]Ba.

16. The pharmaceutical agent according to claim 1, wherein the positron-emitting nuclides are [26]Al.

17. The pharmaceutical agent according to claim 1, wherein the positron-emitting nuclides are [68]Ga.

18. The pharmaceutical agent according to claim 1, wherein the positron-emitting nuclides are [18]F.

19. The pharmaceutical agent according to claim 1, wherein the structure type forming elements consist essentially of amorphous structures.

20. The pharmaceutical agent according to claim 1, wherein the particulate inorganic matrix is selected from the group consisting of topaz $(Al_2F_2)[SiO_4]$, chiolite $Na[Al_3F_4]$, wavellite $Al_3(PO_4)_2(OH,F)_2$, calcium carbonate $(CaCO_3)$, barium sulphate $(BaSO_4)$, gallium phosphate $(GaPO_4)$, apatite or fluorohydroxyapatite $(Ca_5(PO_4)_3(OH,F)=3Ca_3(PO_4)_2*Ca(OH,F)_2)$ and fluorspar $(CaF_2)$.

* * * * *

UNITED STATES PATENT AND TRADEMARK OFFICE
CERTIFICATE OF CORRECTION

PATENT NO. : 8,894,968 B2
APPLICATION NO. : 12/665624
DATED : November 25, 2014
INVENTOR(S) : Kristian Schiling It is certified that error appears in the above-identified patent and that said Letters Patent is hereby corrected as shown below:

On the Title Page Item (57) Abstract, reads:

"The invention relates to pharmaceutical agents containing a particulate inorganic matrix having a diameter of from 0.1 nm to 100 μm, preferably 1 nm to 10 μm, particularly preferably 1 nm to 1 μm, such as, for example, topaz, $(Al_2F_2)[SiO_4]$, and chilite, $Na[Al_3F_4]$, preferably wavellite, $Al_3(PO_4)_2(OH,F)_2$, calcium carbonate, $CaCO_3$, maghemite, $\gamma$-$Fe_2O_3$, particularly preferably zeolites, gen. formula $M_n[(AlO_2)_x(SiO_2)_y]$(M=metal, e.g. Na), magnetite, $Fe_3O_4$, and barium sulphate, $BaSO_4$, and very particularly preferably gallium phosphate, $GaPO_4$, apatite or fluorohydroxyapatite, $Ca_5(PO_4)_3(OH,F)=3Ca_3(PO_4)_2*Ca(OH,F)_2$, and fluorspar, $CaF_2$, which, in addition to the natural isotope distribution of the structure type-forming elements of the anions and cations, also contain medically usable contents of positron-emitting nuclides, such as, for example, $^{15}$O, [30]P, $^{13}$N, preferably [65]Ga, $^{11}$C, particularly preferably [13]Ba, [26]Al, and very particularly preferably $^{68}$Ga and $^{18}$F, the preparation thereof, and the use of these composition in medicine, particularly preferably in diagnostic imaging, in particular positron emission tomography (PET), on animals and humans, and in vitro diagnostics."

Should read:

--The invention relates to pharmaceutical agents containing a particulate inorganic matrix having a diameter of from 0.1 nm to 100 μm, preferably 1 nm to 10 μm, particularly preferably 1 nm to 1 μm, such as, for example, topaz, $(Al_2F_2)[SiO_4]$, and chilite, $Na[Al_3F_4]$, preferably wavellite, $Al_3(PO_4)_2(OH,F)_2$, calcium carbonate, $CaCO_3$, maghemite, $\gamma$-$Fe_2O_3$, particularly preferably zeolites, gen. formula $M_n[(AlO_2)_x(SiO_2)_y]$(M=metal, e.g. Na), magnetite, $Fe_3O_4$, and barium sulphate, $BaSO_4$, and very particularly preferably gallium phosphate, $GaPO_4$, apatite or fluorohydroxyapatite, $Ca_5(PO_4)_3(OH,F)=3Ca_3(PO_4)_2*Ca(OH,F)_2$, and fluorspar, $CaF_2$, which, in addition to the natural isotope distribution of the structure type-forming elements of the anions and cations, also contain medically usable contents of positron-emitting nuclides, such as, for example, $^{15}$O, [30]P, $^{13}$N, preferably [65]Ga, $^{11}$C, particularly preferably [131]Ba, [26]Al, and very particularly preferably $^{68}$Ga and $^{18}$F, the preparation thereof, and the use of these composition in medicine, Signed and Sealed this
Nineteenth Day of May, 2015

Michelle K. Lee
*Director of the United States Patent and Trademark Office* particularly preferably in diagnostic imaging, in particular positron emission tomography (PET), on animals and humans, and in vitro diagnostics.--